(12) United States Patent
Lange

(10) Patent No.: US 8,286,513 B2
(45) Date of Patent: Oct. 16, 2012

(54) BOAT INCLUDING AUTOMATED WATER SAMPLING DEVICE AND METHOD OF USING THE SAME

(75) Inventor: Carl J. Lange, Uniondale, NY (US); Frances Lange, legal representative, Uniondale, NY (US)

(73) Assignee: Brooklyn Tech Alumni Foundation, Brooklyn, NY (US)

( * ) Notice: Subject to any disclaimer, the term of this patent is extended or adjusted under 35 U.S.C. 154(b) by 471 days.

(21) Appl. No.: 12/559,991

(22) Filed: Sep. 15, 2009

(65) Prior Publication Data
US 2010/0095789 A1    Apr. 22, 2010

Related U.S. Application Data

(63) Continuation-in-part of application No. 12/210,586, filed on Sep. 15, 2008.

(60) Provisional application No. 61/097,011, filed on Sep. 15, 2008.

(51) Int. Cl.
*G01N 1/12*    (2006.01)

(52) U.S. Cl. ................................. 73/864.63; 73/846.67
(58) Field of Classification Search ............... 73/863.31, 73/864.63
See application file for complete search history.

(56) References Cited

U.S. PATENT DOCUMENTS

| 4,554,826 A * | 11/1985 | Barry ........................ 73/170.34 |
| 5,404,763 A * | 4/1995 | Guggenheim ............. 73/863.31 |
| 7,967,149 B2 * | 6/2011 | Helgi ............................ 209/592 |

* cited by examiner

*Primary Examiner* — Hezron E Williams
*Assistant Examiner* — Nashmiya Fayyaz
(74) *Attorney, Agent, or Firm* — F. Chau & Associates, LLC; Michael F. Morano

(57) ABSTRACT

A water sampling device comprises a cylinder, a first disk positioned at a top of the cylinder, a plurality of sampling tubes attached to the first disk, and a second disk positioned on the first disk, wherein the second disk includes an aperture through which water to be sampled flows into one of the plurality of sampling tubes when the aperture is lined up with an opening of the one sampling tube.

12 Claims, 16 Drawing Sheets

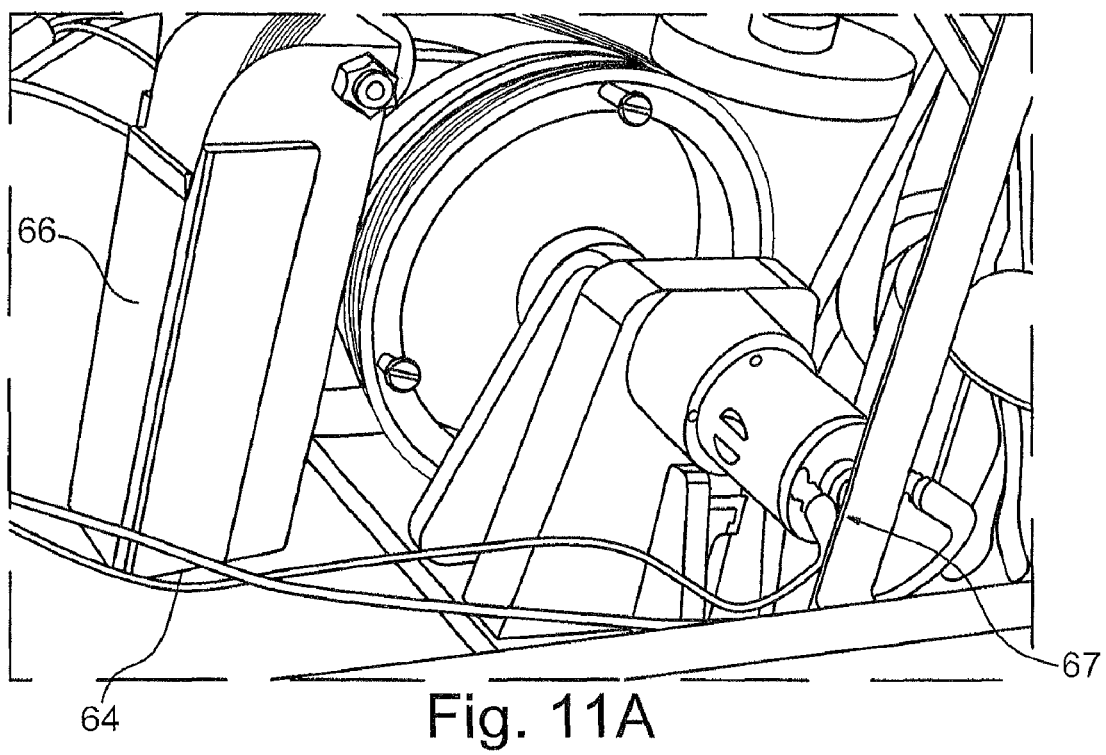
Fig. 11A
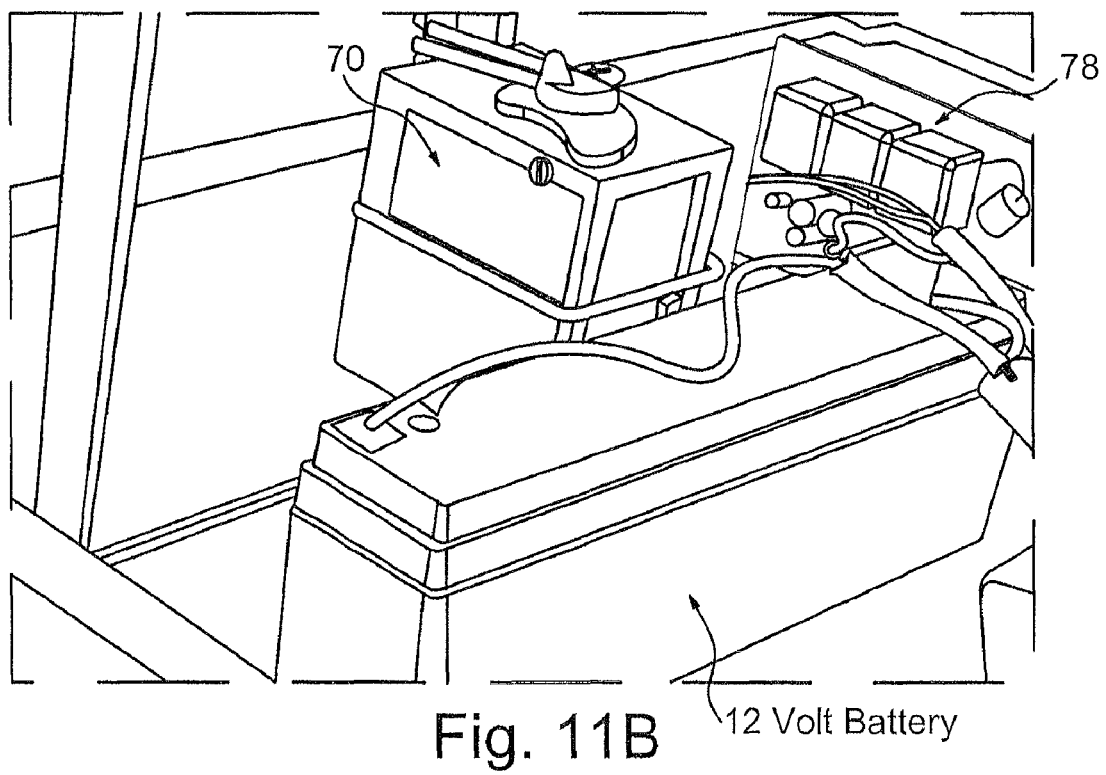
Fig. 11B — 12 Volt Battery

BOAT INCLUDING AUTOMATED WATER SAMPLING DEVICE AND METHOD OF USING THE SAME

CROSS-REFERENCE TO RELATED APPLICATIONS

This application claims the benefit of U.S. Provisional Patent Application Ser. No. 61/097,011, filed on Sep. 15, 2008, the contents of which are herein incorporated by reference in their entirety.

This application is a continuation-in-part of U.S. patent application Ser. No. 12/210,586, filed on Sep. 15, 2008, which claims the benefit of U.S. Provisional Patent Application Ser. No. 60/972,671, filed on Sep. 14, 2007, the contents of which are herein incorporated by reference in their entirety.

BACKGROUND OF THE INVENTION

1. Technical Field

The present disclosure relates to an automated water sampling device for a boat, and a method of using same.

2. Discussion of the Related Art

Water sampling to test water quality of bodies of water, such as oceans, rivers, lakes, ponds and streams is vital to environmental studies to assess critical features, such as whether water is safe for consumption, swimming, and watering crops.

Known methods and devices for testing water require that a human tester manually retrieve samples of water by submerging a can including a vial or container to collect the sample. The human testers typically must position themselves at various points on the body of water to take single samples from different locations.

To ensure accuracy, the known devices and processes require that the testers change their location on the body of water for each sample they take so that a range of samples from different parts of the body of water can be collected. This process is cumbersome and time consuming.

Accordingly, there is need for a device to automatically or semi-automatically collect samples at various positions on a body of water.

SUMMARY OF THE INVENTION

Embodiments of the present invention provide an automated water sampling boat capable to taking samples of water at diverse depths and latitudes, in bodies of water, such as, oceans, lakes, streams, ponds and rivers.

A water sampling device, according to an embodiment of the present invention, comprises a cylinder, a first disk positioned at a top of the cylinder, a plurality of sampling tubes attached to the first disk, and a second disk positioned on the first disk, wherein the second disk includes an aperture through which water to be sampled flows into one of the plurality of sampling tubes when the aperture is lined up with an opening of the one sampling tube.

The second disk may rotate to line up the aperture with the opening of the one sampling tube. Water to be sampled may flow into another of the plurality of sampling tubes when the aperture is lined up with an opening of the other sampling tube. The second disk may rotate the aperture away from the opening of the one sampling tube to line up the aperture with the opening of the other sampling tube.

The second disk may be coupled to a shaft rotated by a remotely controlled motor.

The first disk may be fixed to the cylinder and remain stationary while the second disk rotates.

The water sampling device may further comprise a timing mechanism controlling rotation of the second disk, the timing mechanism comprising a first conductive strip, and a second conductive strip, wherein the second conductive strip is perforated by a plurality of apertures creating non-conductive spaces between non-perforated portions of the second conductive strip. The timing mechanism may further comprise a first contact contacting the first conductive strip, and a second contact alternately contacting the second conductive strip and the non-conductive spaces.

The water sampling device may further comprise a motor for rotating the second disk, wherein the motor is disengaged when the second contact contacts a non-conductive space.

The plurality of sampling tubes may be attached to the first disk at a side opposite to the side on which the second disk is positioned on the first disk.

A method for water sampling, according to an embodiment of the present invention, comprises positioning a first disk at a top of a cylinder, wherein a plurality of sampling tubes are attached the first disk and extend from an underside of the first disk, positioning a second disk on a top side of the first disk, wherein the second disk includes an aperture, lining up the aperture with an opening in one of the plurality of sampling tubes, and submerging the cylinder to allow water to be sampled to flow through the aperture into the opening of the one sampling tube.

The method may further comprise rotating the second disk to line up the aperture with the opening of the one sampling tube. The second disk may be further rotated to move the aperture away from the opening of the one sampling tube to line up the aperture with an opening of another of the plurality of sampling tubes. A motor may be remotely controlled to rotate a shaft coupled to the second disk.

Rotation of the second disk may be controlled by a timing mechanism comprising a conductive strip perforated by a plurality of apertures creating non-conductive spaces between non-perforated portions of the conductive strip.

The method may further comprise alternately positioning an electrical contact to contact the conductive strip and the non-conductive spaces, wherein a motor for rotating the second disk is disengaged when the electrical contact contacts a non-conductive space.

BRIEF DESCRIPTION OF THE DRAWINGS

Exemplary embodiments of the present invention will be described below in more detail, with reference to the accompanying drawings, of which:

FIGS. 10A, 10B, 11A, 12B 13A and 15B are perspective views of a winch, according to an embodiment of the present invention;

FIGS. 11B, 14A, 14B and 15A are perspective views of a steering mechanism according to an embodiment of the present invention;

DETAILED DESCRIPTION OF EXEMPLARY EMBODIMENTS

Exemplary embodiments of the present invention now will be described more fully hereinafter with reference to the accompanying drawings. This invention may, however, be embodied in many different forms and should not be construed as limited to the embodiments set forth herein.

Figure 1:
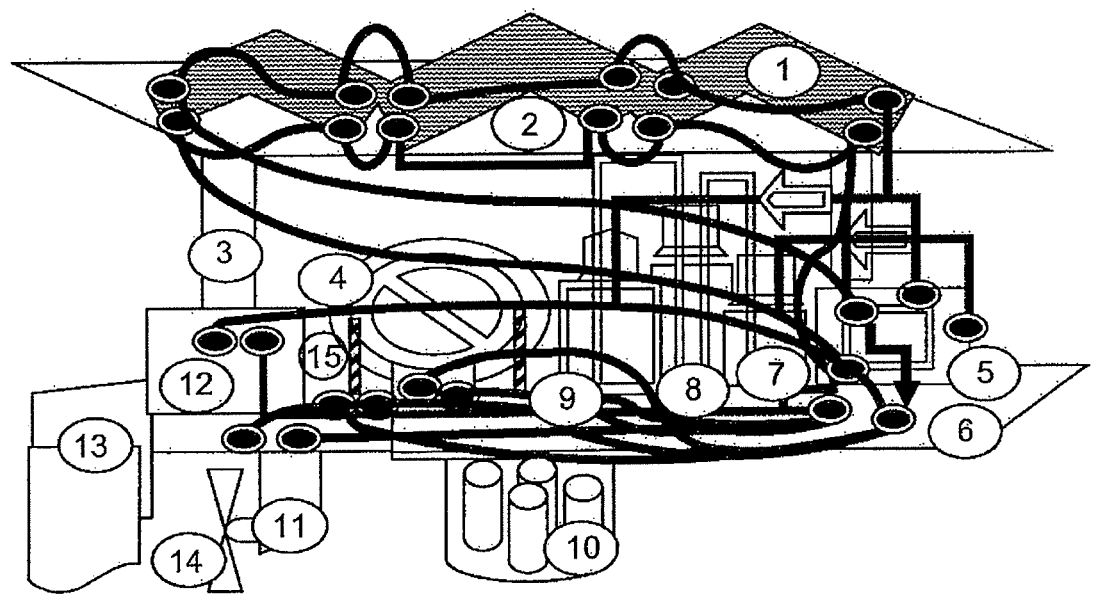
FIG. 1 is a schematic diagram of an automated water sampling boat, according to an embodiment of the present invention.
Figure 2:
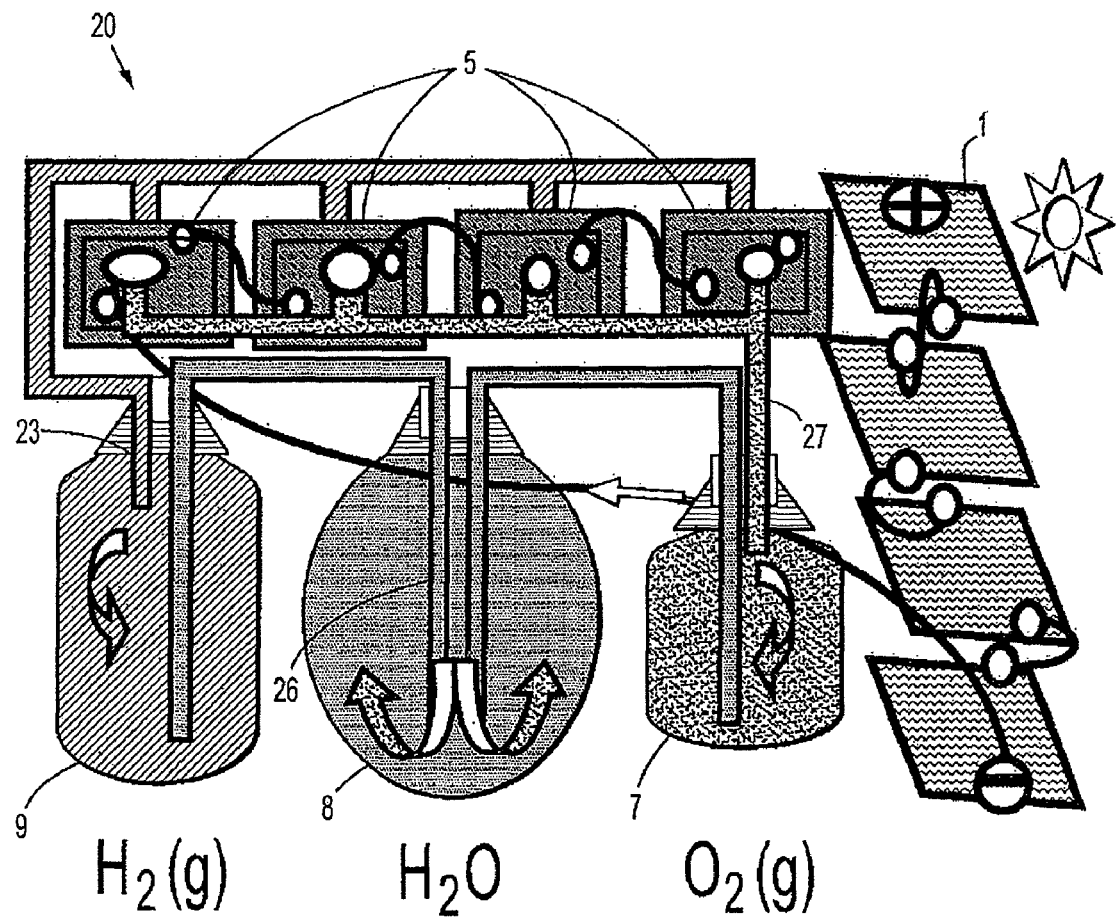
FIG. 2 is a schematic diagram of a solar hydrogen electrochemical reactor, according to an embodiment of the present invention.
Figure 3:
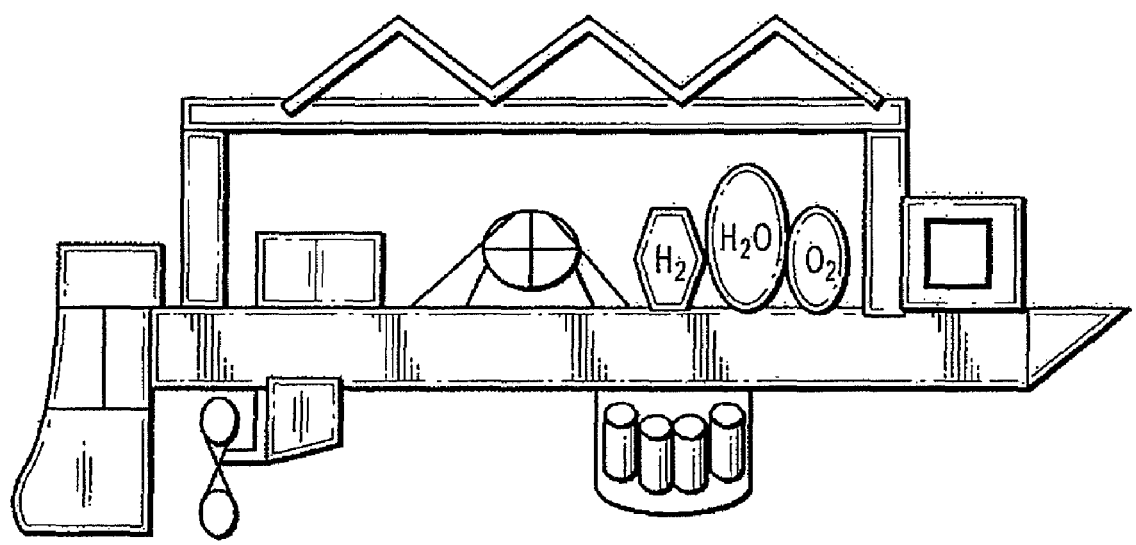
FIG. 3 is a side view of an automated water sampling boat, according to an embodiment of the present invention.
Figure 4A:
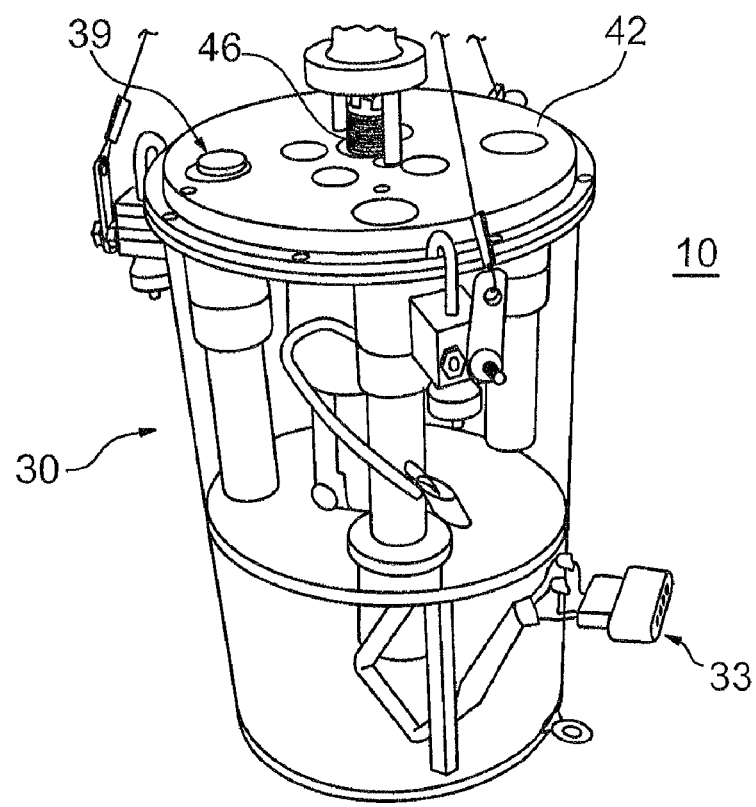
FIGS. 4A-4B, 5A-5B, 6A-6B, 7A-7B and 8A-8B are perspective views of a cylindrical probe, according to an embodiment of the present invention.
Figure 4B:
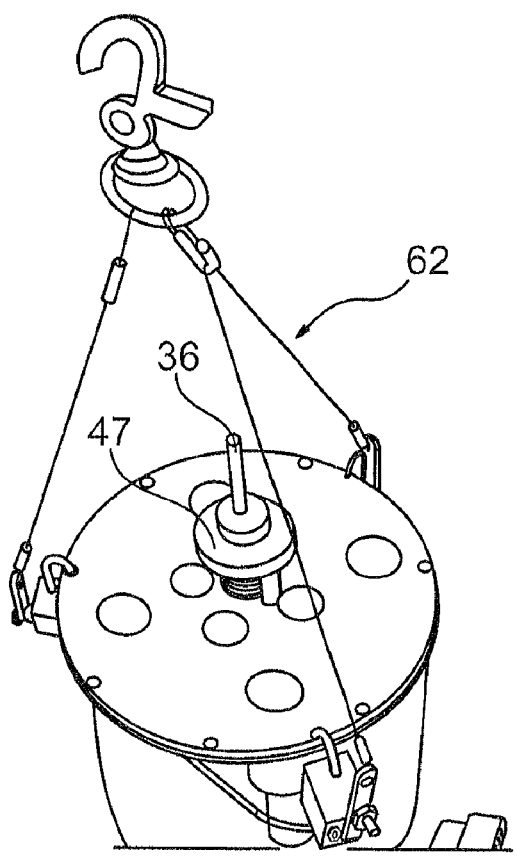
Figure 5A:
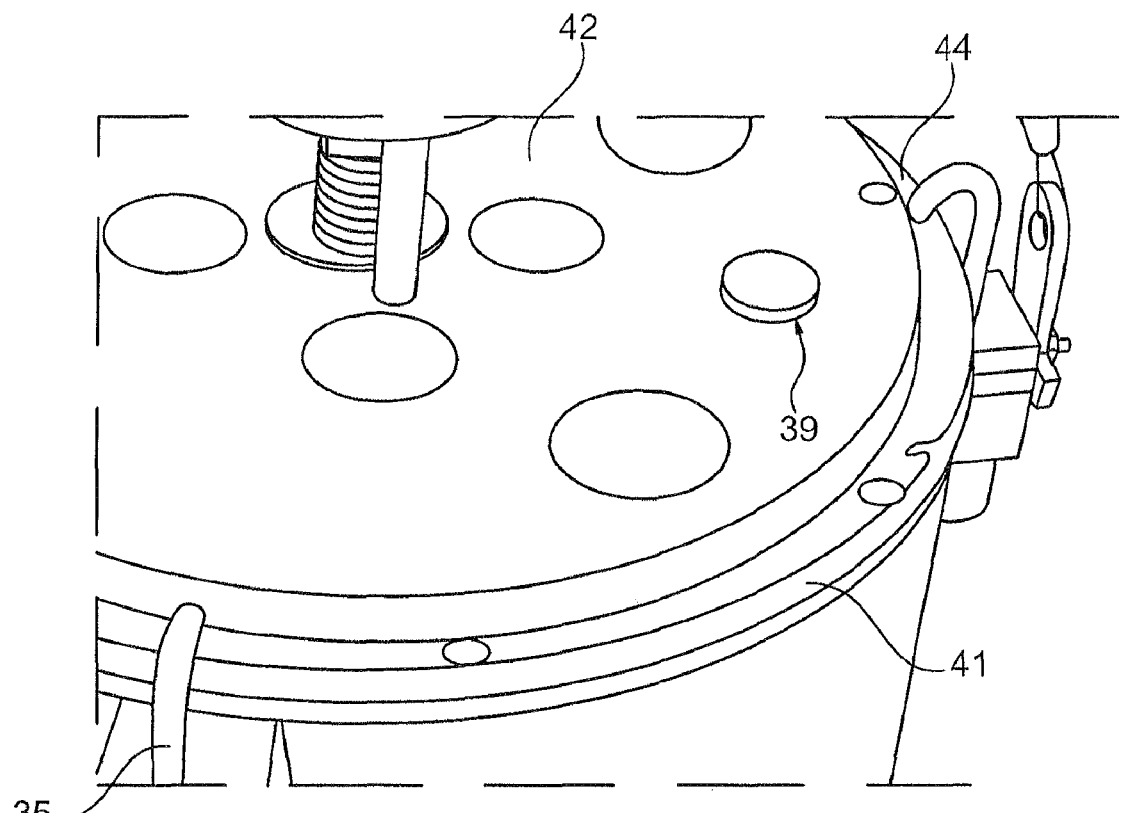
Figure 5B:
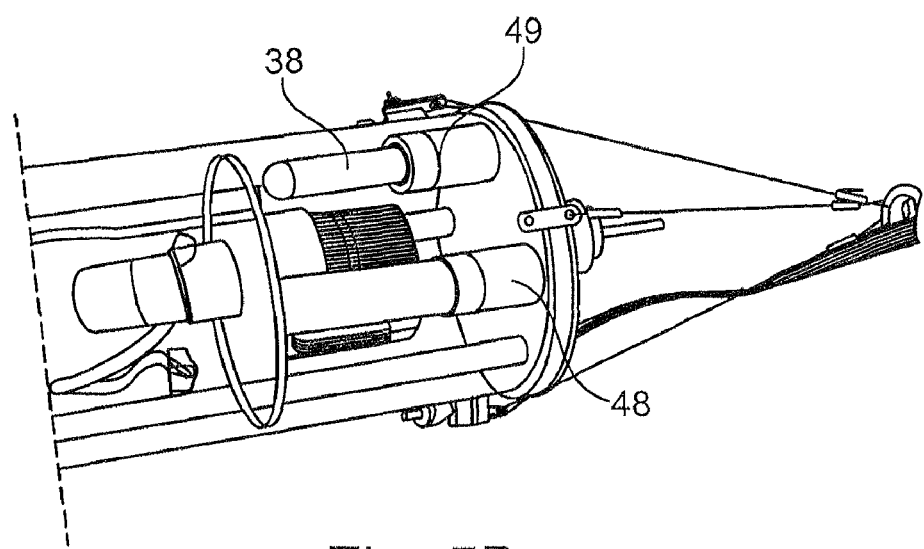
Figure 6A:
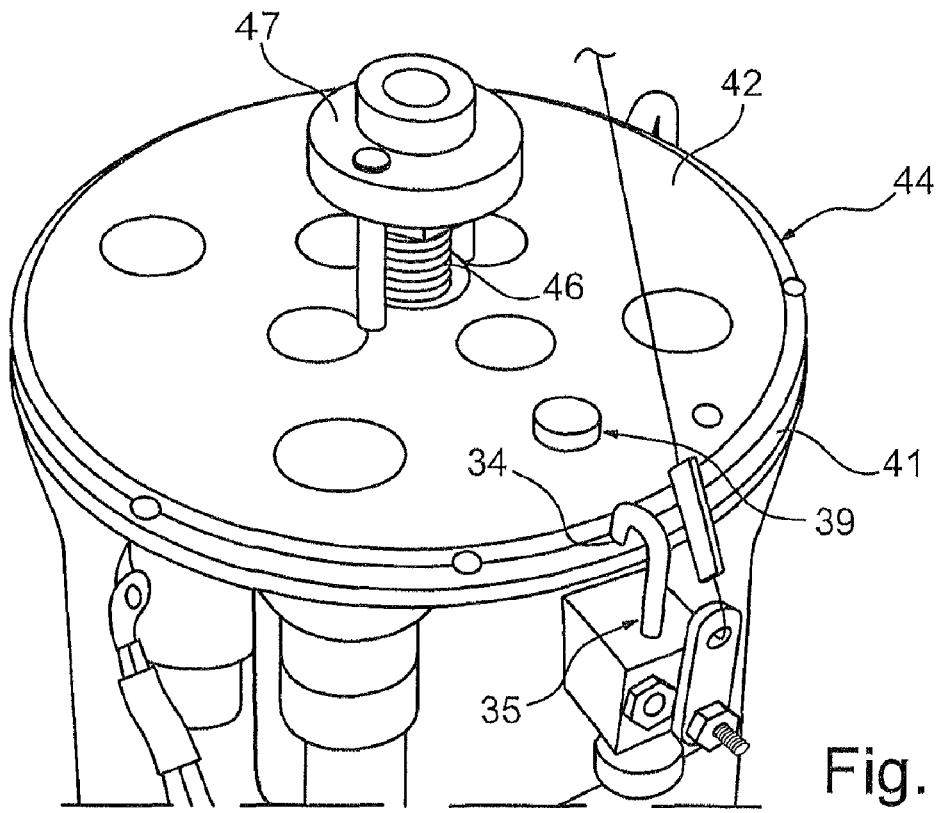
Figure 6B:
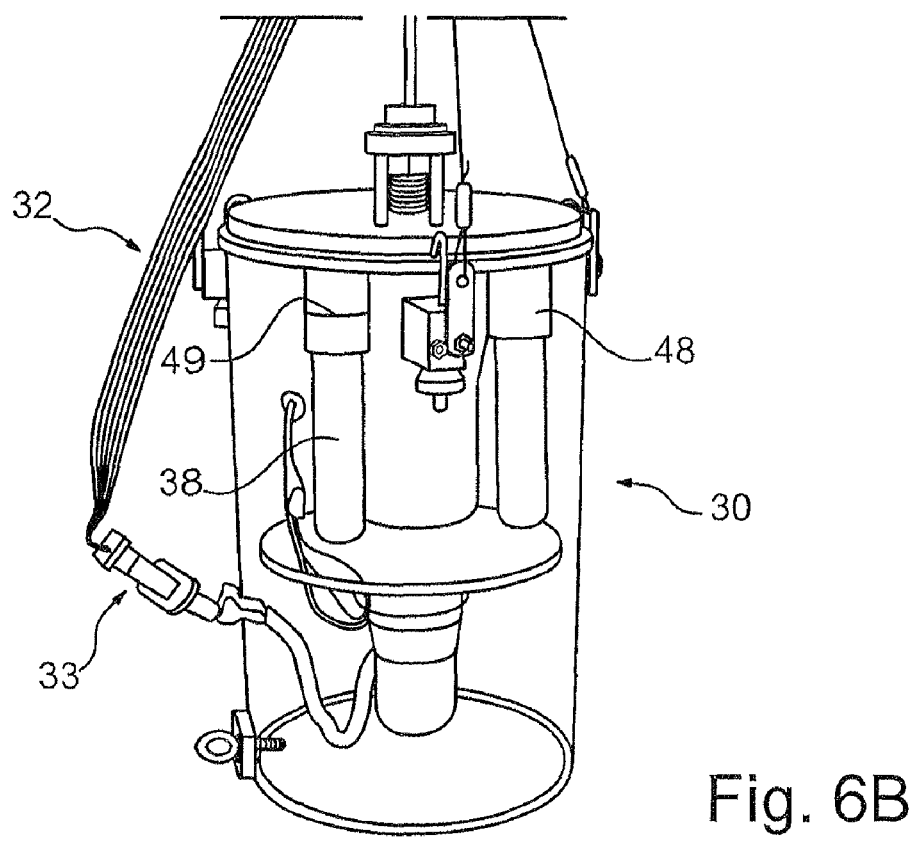
Figure 7A:
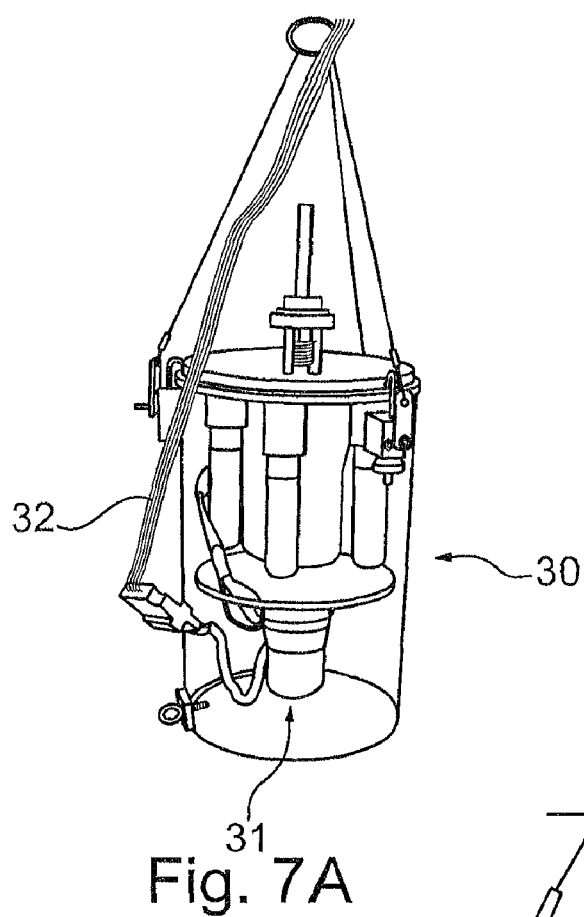
Figure 7B:
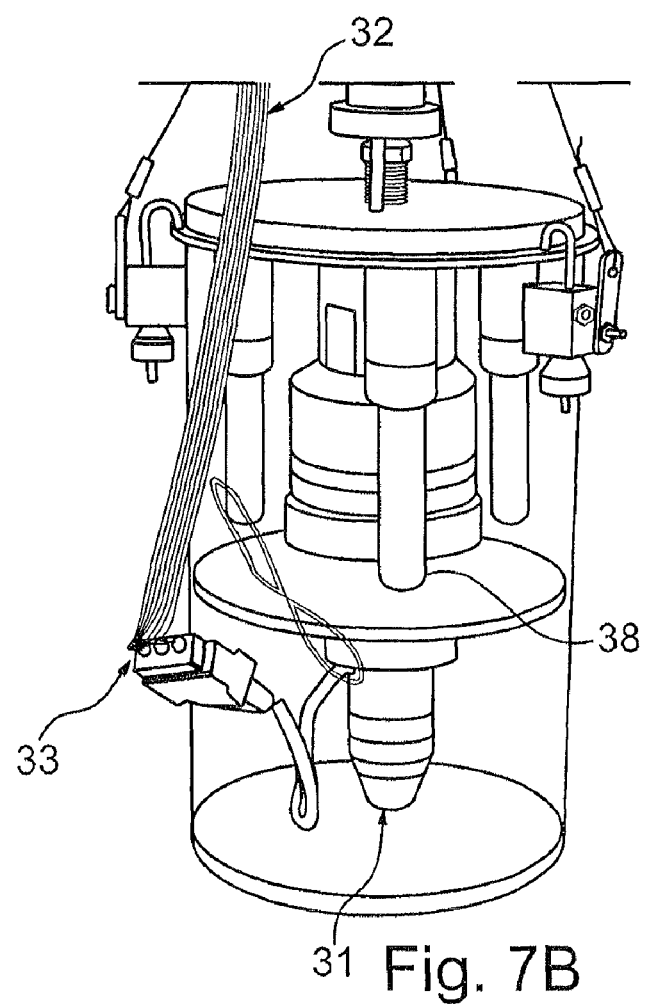
Figure 8A:
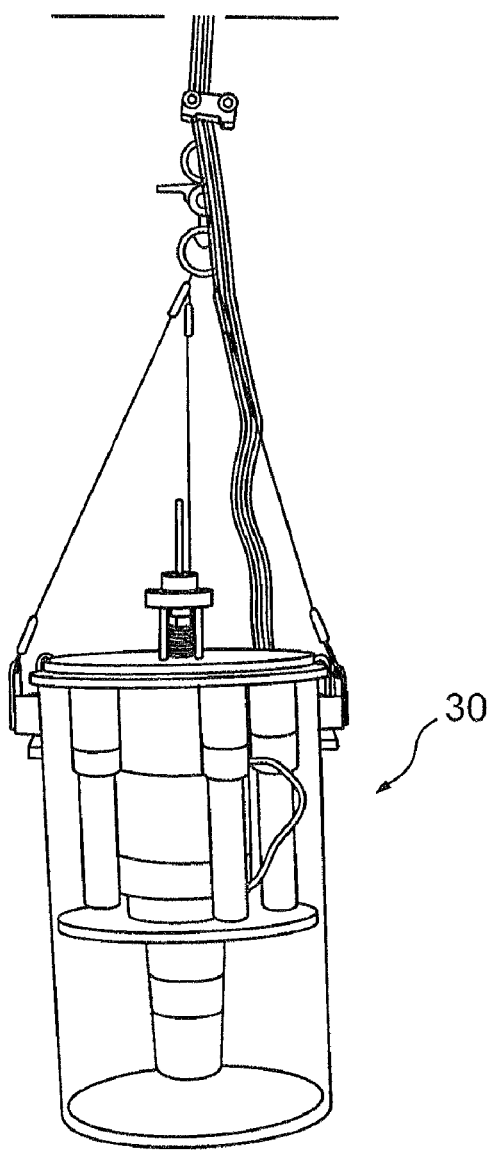
Figure 8B:
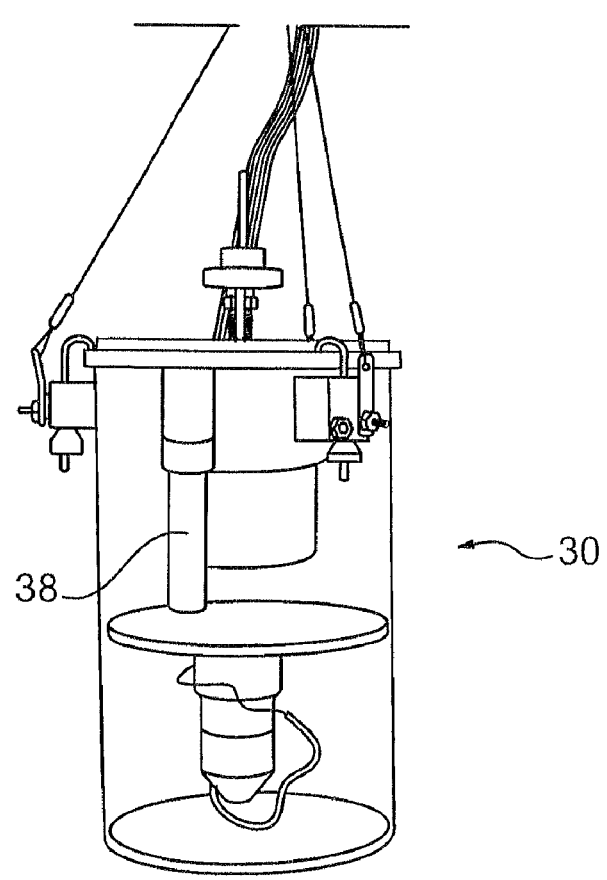

Referring to FIGS. 1-3, an automated water sampling boat includes a plurality of solar panels 1 positioned on a roof 2 of the boat. The roof 2 may be made of, for example, aluminum. The roof may be supported by a plurality of vertical supports or columns 3, which are connected to a hull 6. The boat includes a propeller support 11, a propeller 14 and a propeller motor 15. A shaft is used to connect the propeller motor 15 to the propeller. The boat also includes a rudder 13 and a rudder motor 12 for moving the rudder 13 to an appropriate position to steer the boat in a particular direction.

According to an embodiment, the boat is unmanned and is controlled from the shore by a multi-channel radio control unit. The multi-channel radio control unit may be used to remotely control all functions of the boat, including operation of the propeller 14 and propeller motor 15, operation of the rudder 13 and rudder motor 12, and operation of the winch 4. Alternatively, the functions of the boat may be pre-programmed to run a sampling operation controlled by a computer, and a global positioning system (GPS) may be utilized.

In operation, the boat is used to collect water samples at a variety of depths and latitudes in a body of water. A robotic winch 4, with a water sampling probe 10 attached thereto, lowers the water sampling probe 10, from below the boat, to a variety of depths to collect a plurality of water samples. The probe 10 consists of a cylinder containing a plurality of detachable test tubes, such as, for example, four test-tubes, attached/mounted below a rotating disc, which rotates about the vertical axis. The disc when rotated can position the mouth of each test-tube below an aperture at the top of the cylinder through which water flows from a sub-surface segment of a body of water. The aperture is positioned over a single test-tube to take a sample, while the remaining test-tubes do not collect a sample.

Referring to FIGS. 4A-15B, the probe 10 includes a cylinder 30 housing drive motor 31, which receives power from the surface of the boat through an electrical cable 32 connected to an electrical input receptacle 33. The electrical cable 32 and the connection via the electrical input receptacle 33 are waterproof.

According to an embodiment of the present invention, the cylinder 30 is made of Plexiglas, with a radius of 13.5 cm and a height of 30 cm, and includes a bottom panel cemented to the cylinder 30. The top of the cylinder 30 includes a double lid 40, including two disks 41 and 42 and a Teflon seal 44 interposed between the disks 41 and 42. A plurality of equally spaced apertures 34 are located around the circumference of the bottom disk 41. A plurality of hooks 35 are respectively inserted in each of the apertures 34. The bases of each of the hooks 35 have screw threads which are used for tightly sealing the disks 41 and 42 together and to the cylinder 30 creating a water tight device. A shaft 36 is located at the center of the disks 41 and 42 and extends from the outside into the lower portion of the cylinder 30. The shaft 36, once coupled to a drive motor 31, rotates the top disk 42 to line up one of the plurality of test/sampling tubes 38 with an access port aperture 39, through which water to be sampled flows into the test/sampling tube 38. The access port aperture 39 is an opening in the upper disk 42 that when rotated provides a passage for water sample entry into a storage tube 38 that is lined up with the access port aperture.

The drive motor 31 can be, for example, a 12 volt, 110 milliamp motor, and is inside the lower half of the cylinder 30. At the upper end of the shaft 36, is a compression spring 46 with a cap 47 for maintaining pressure on the lid 40. The plurality of sampling tubes 38, for example, four (4) test tubes, are positioned on the lower disk 41. The tubes 38 are retained in Plexiglas tubes 48 containing rubber O rings 49. The Plexiglas tubes 48 are cemented to the lower disk 41. A pulsed current rotates the upper disk 42 such that the mouth of a test tube 38 is perfectly aligned with the access port aperture 39 in the upper disk 42, which serves as the entrance of a sample of water from a water source. Once the tube 38 is filled, the upper disk 42 rotates to a closed position closing the access port aperture 39 to prevent water from entering the cylinder 30. Another pulsed current then rotates the upper disk 42 and the access port aperture 39 to the mouth of another test tube 38, which is perfectly aligned for collecting another water sample. Each sample can be collected in a different location and at different depths by lowering or raising the water sampler, using a remote control channel that operates the winch 4 which is mounted in the surface vessel.

The cylinder 30 is physically and electrically connected to the surface vessel by a ribbon type multi conductor wire 32. The ribbon wire 32 is marked at intervals of 15 cm and is calibrated such that the depth of submergence of the sampler can be calculated.

The ribbon wire 32 is connected to positive and negative leads on the vessel on the surface of the water and connected to the electrical input receptacle 33 under the water. The leads into the electrical input receptacle 33 provide the power and control of the drive motor 31 within the cylinder 30 that rotates the upper disk 42 to line up the access port aperture 39 with the sample tubes 38. The cylinder is further supported by a plurality of support lines 62 connected at predetermined points around the circumference of the cylinder 30. A holder 63 for the support lines 62 is mounted to the ribbon wire 32 exiting through a hole 64 in the bottom of the boat. A hook 65 may be used to connect the support lines 62 to the holder 63.

The ribbon wire 32 runs up through the hole 64 through a conduit 66 and around a circular support 68 mounted to the conduit 66 to the winch 4. The ribbon wire 32 and support line 62 entwined in parallel with the ribbon wire 32, is wound around the spool of the winch 4. The ribbon wire 32 and support line 62 may measure more than 3 meters. A winch drive motor 67 drives the winch 4 to rotate the winch 4 to wrap or unwrap the ribbon wire 32 and support line 62 around the winch drum for raising and lowering the cylinder 30. Connection to the winch 4 to the remote control can be provided via an electrically conductive winch contact plate 69 connected to contacts 79 extending from the radio control module 78.

Figure 9A:
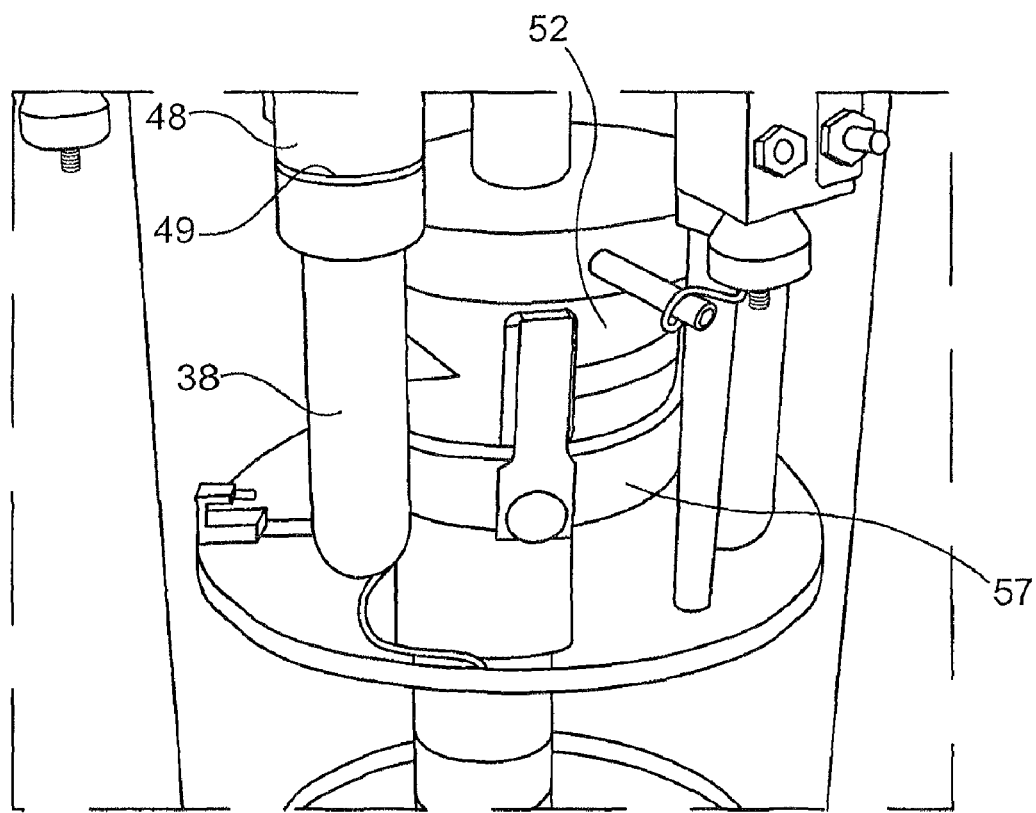
FIGS. 9A-9B are perspective views of a timing mechanism, according to an embodiment of the present invention.
Figure 9B:
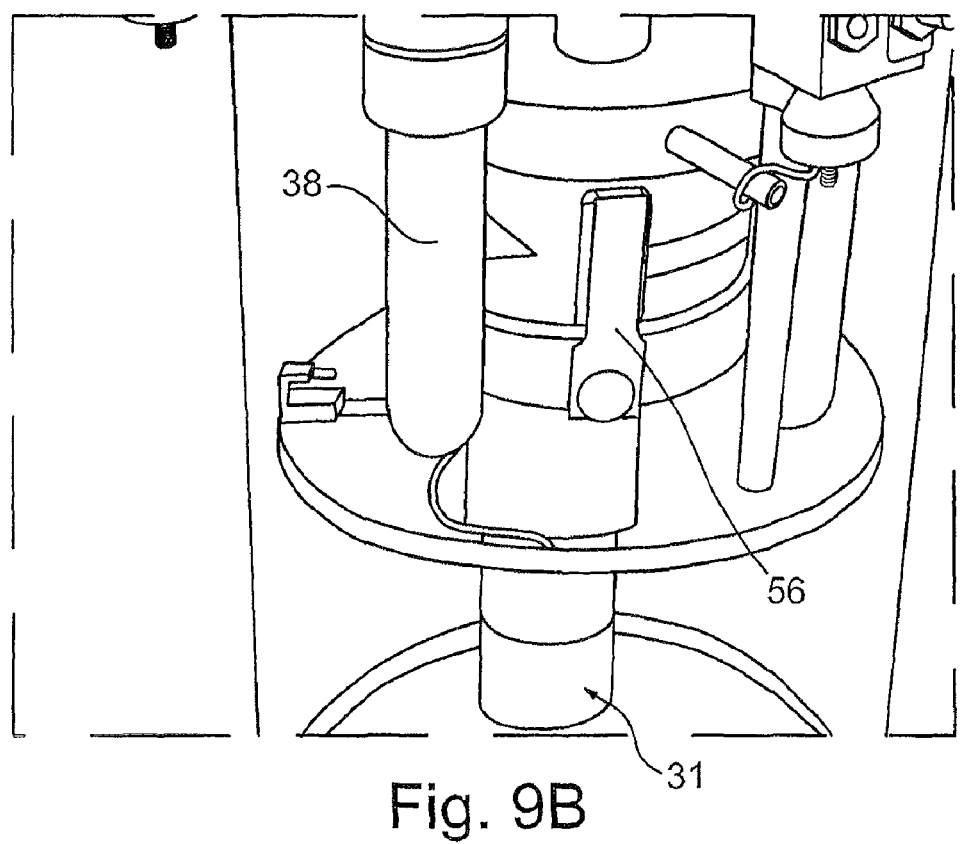
Figure 10A:
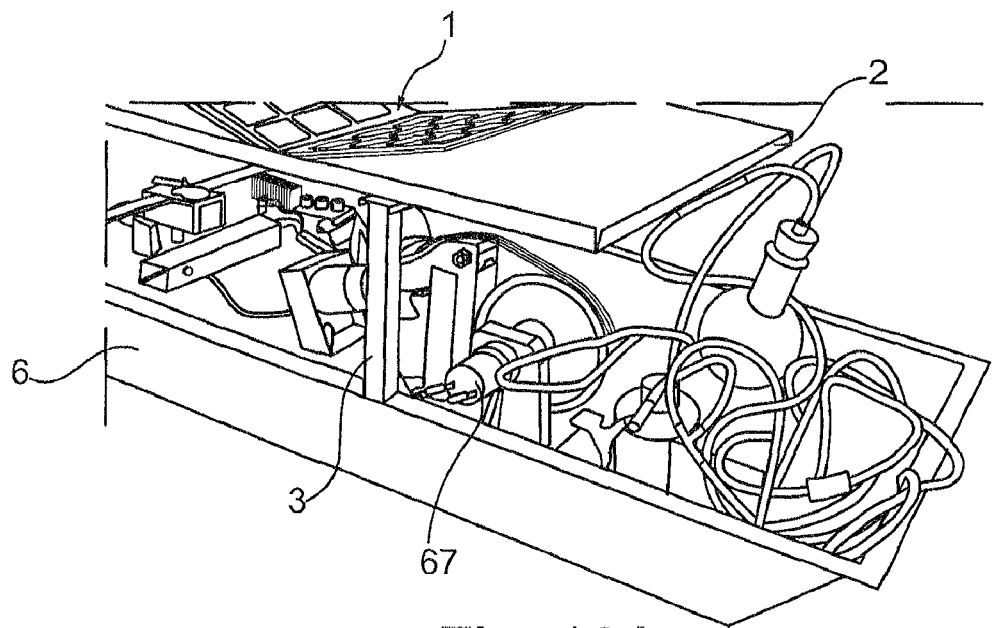
Figure 10B:
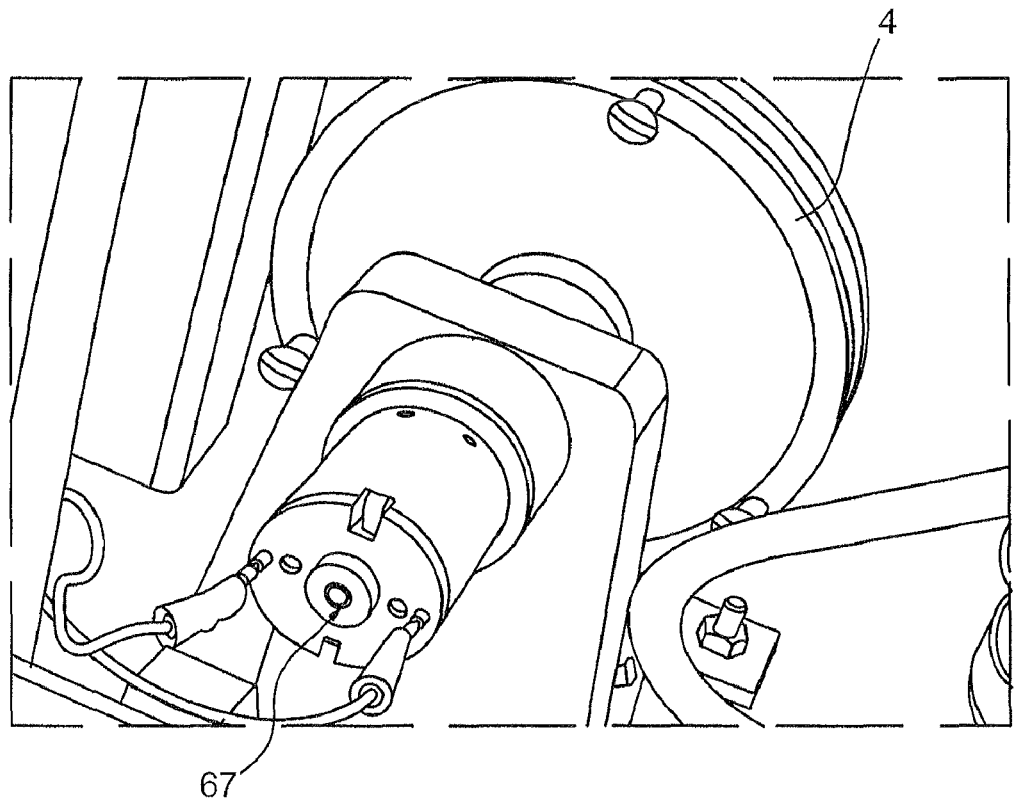
Figure 12A:
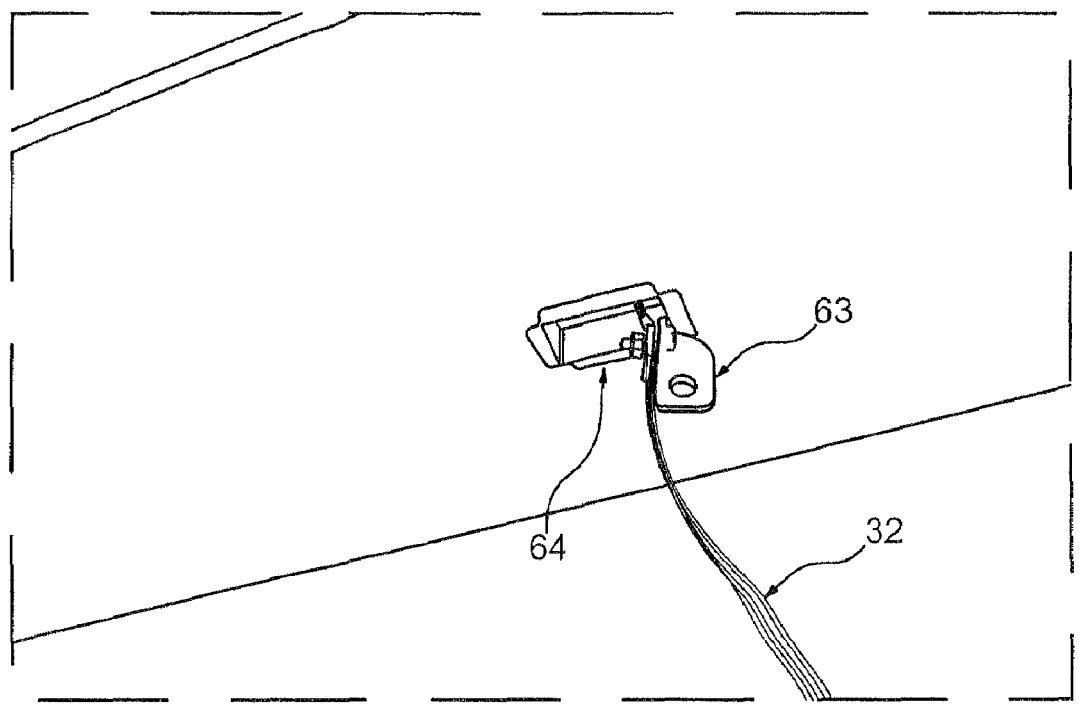
FIG. 12A is a perspective view of a bottom side of the boat, according to an embodiment of the present invention.
Figure 12B:
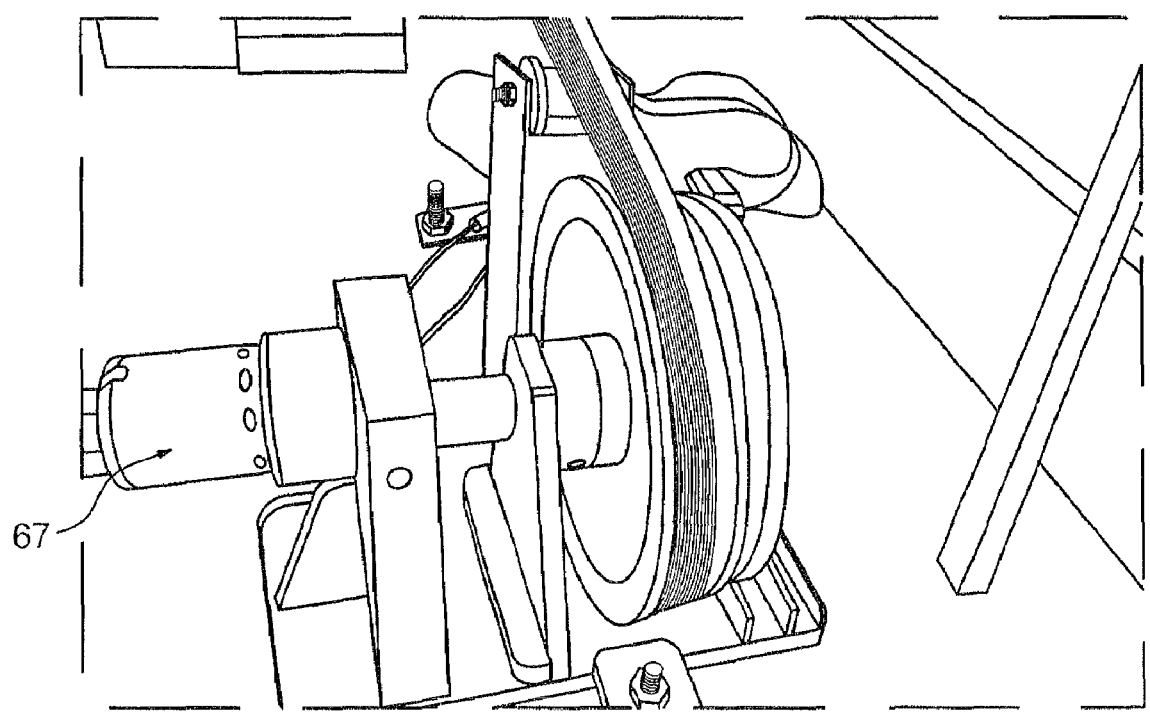
Figure 13A:
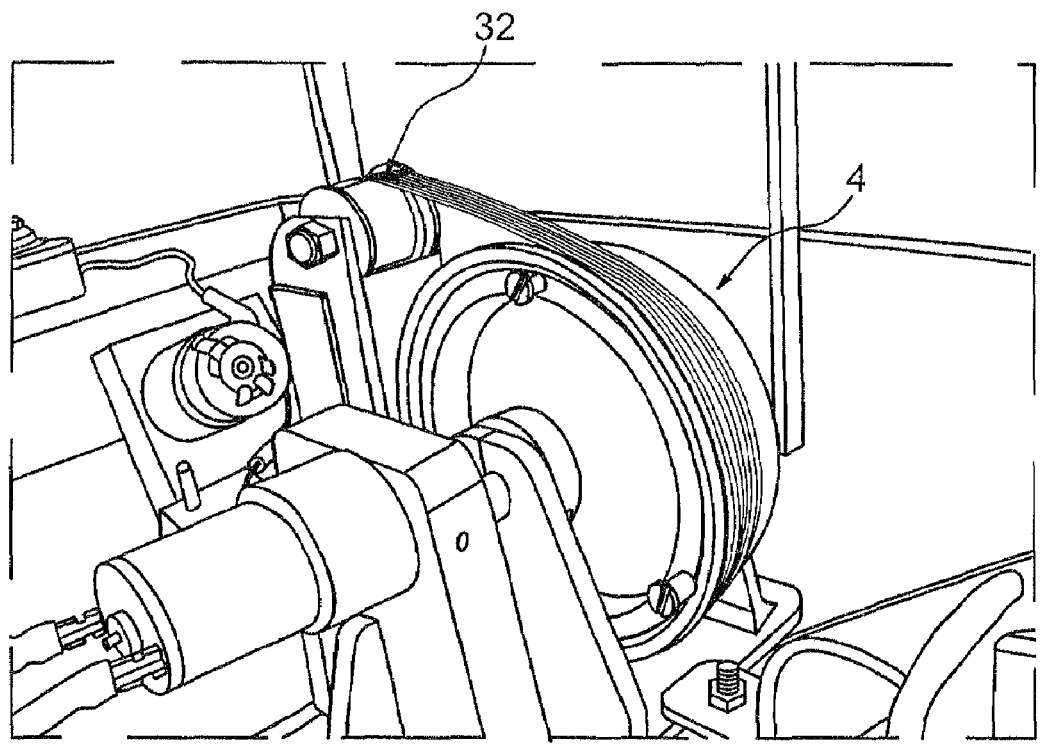
Figure 13B:
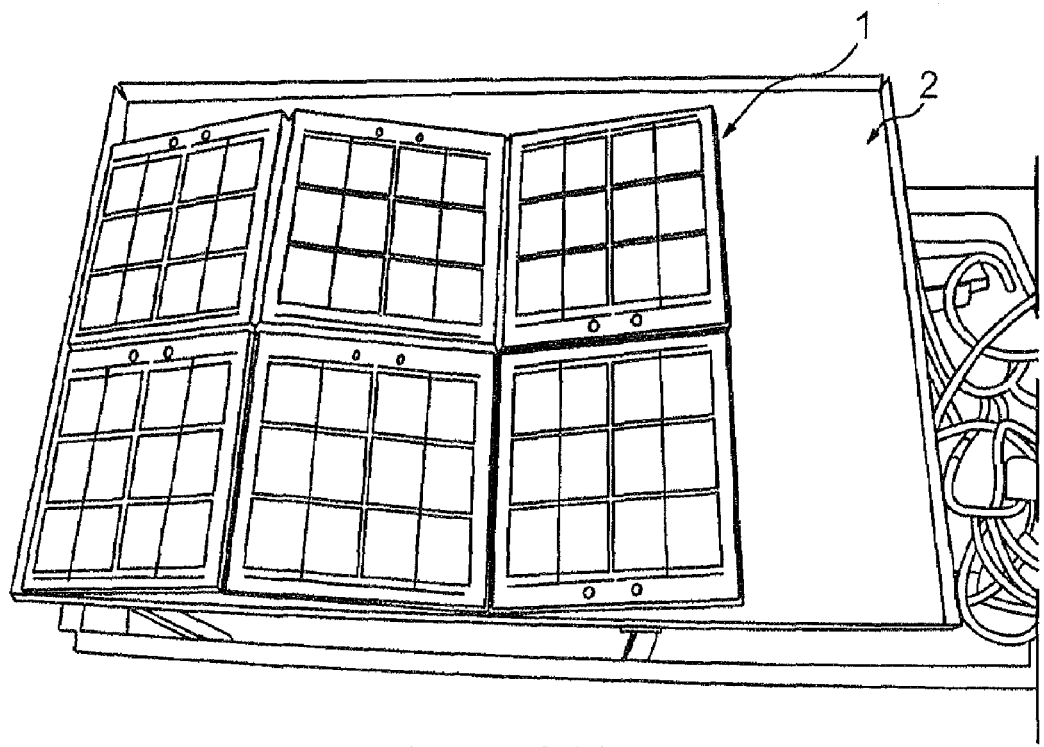
FIG. 13B is a perspective view of solar panels positioned on an upper portion of a boat, according to an embodiment of the present invention.
Figure 14A:
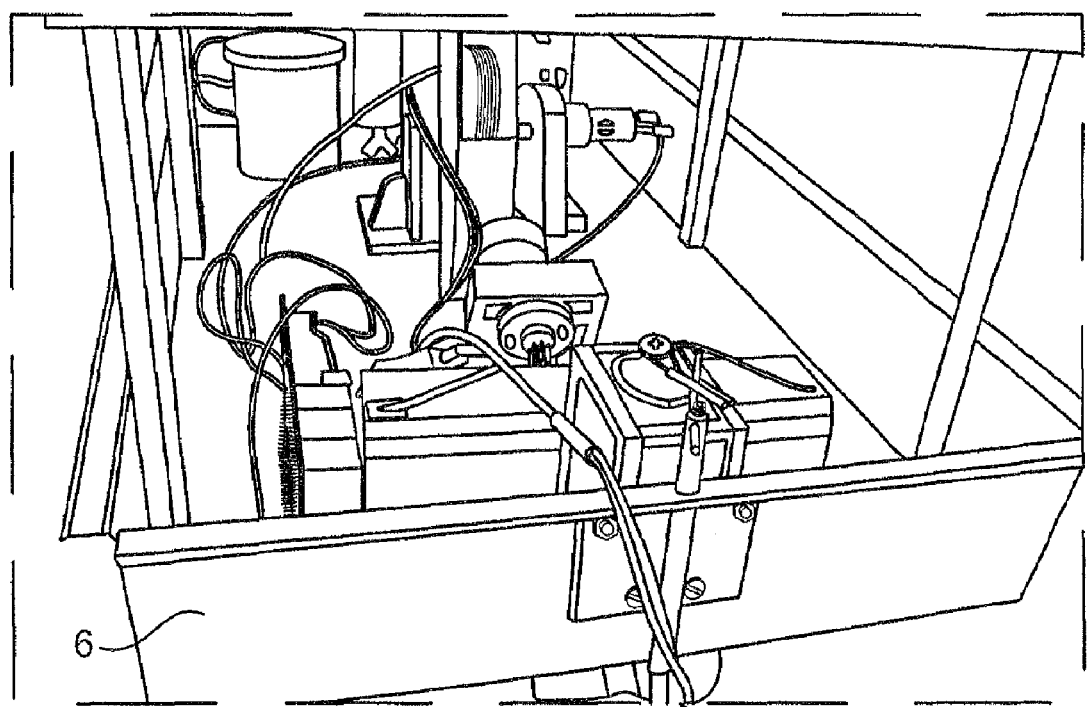
Figure 14B:
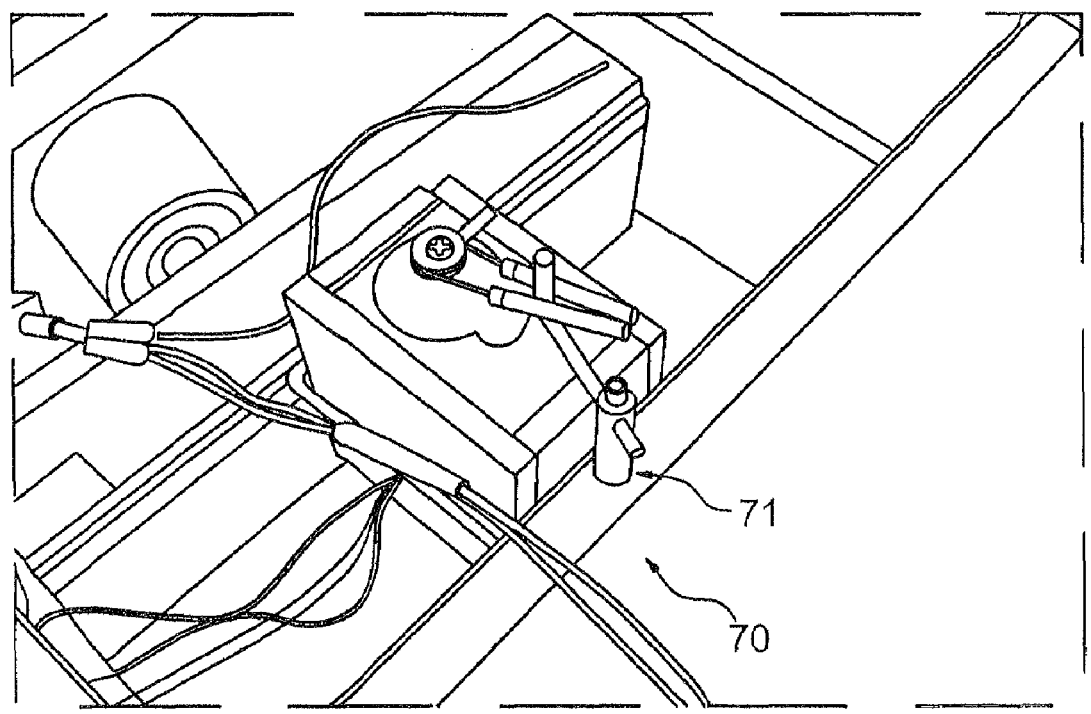
Figure 15A:
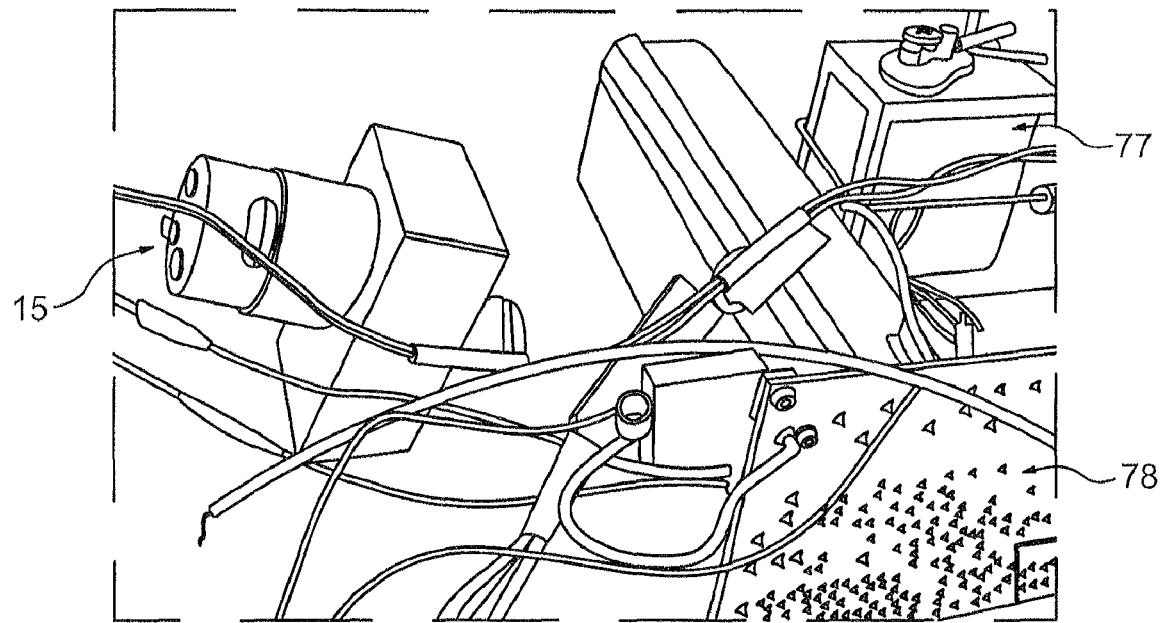
Figure 15B:
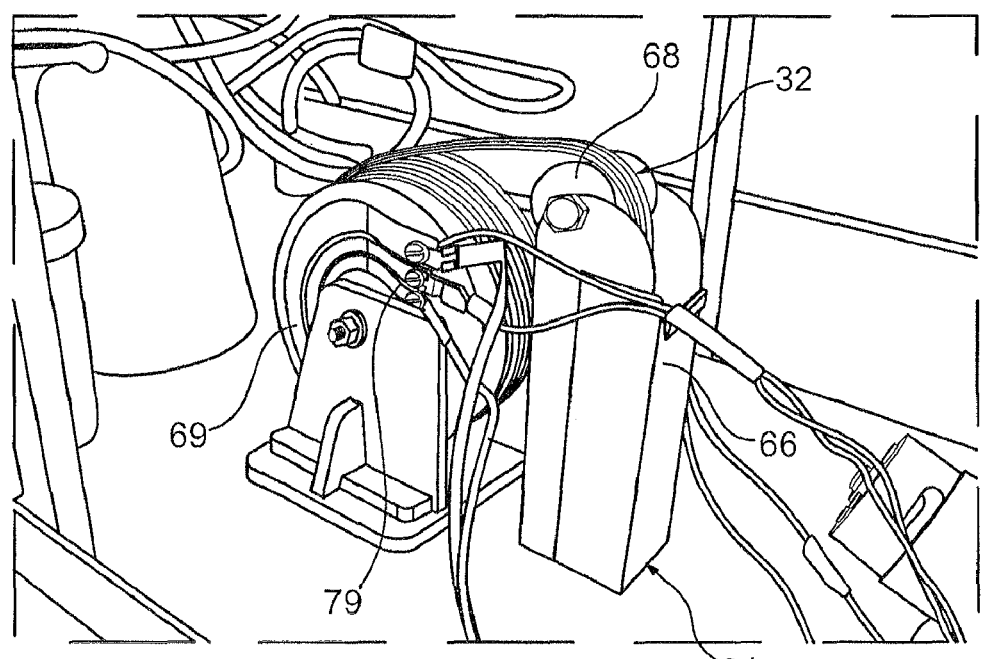
Figure 16:
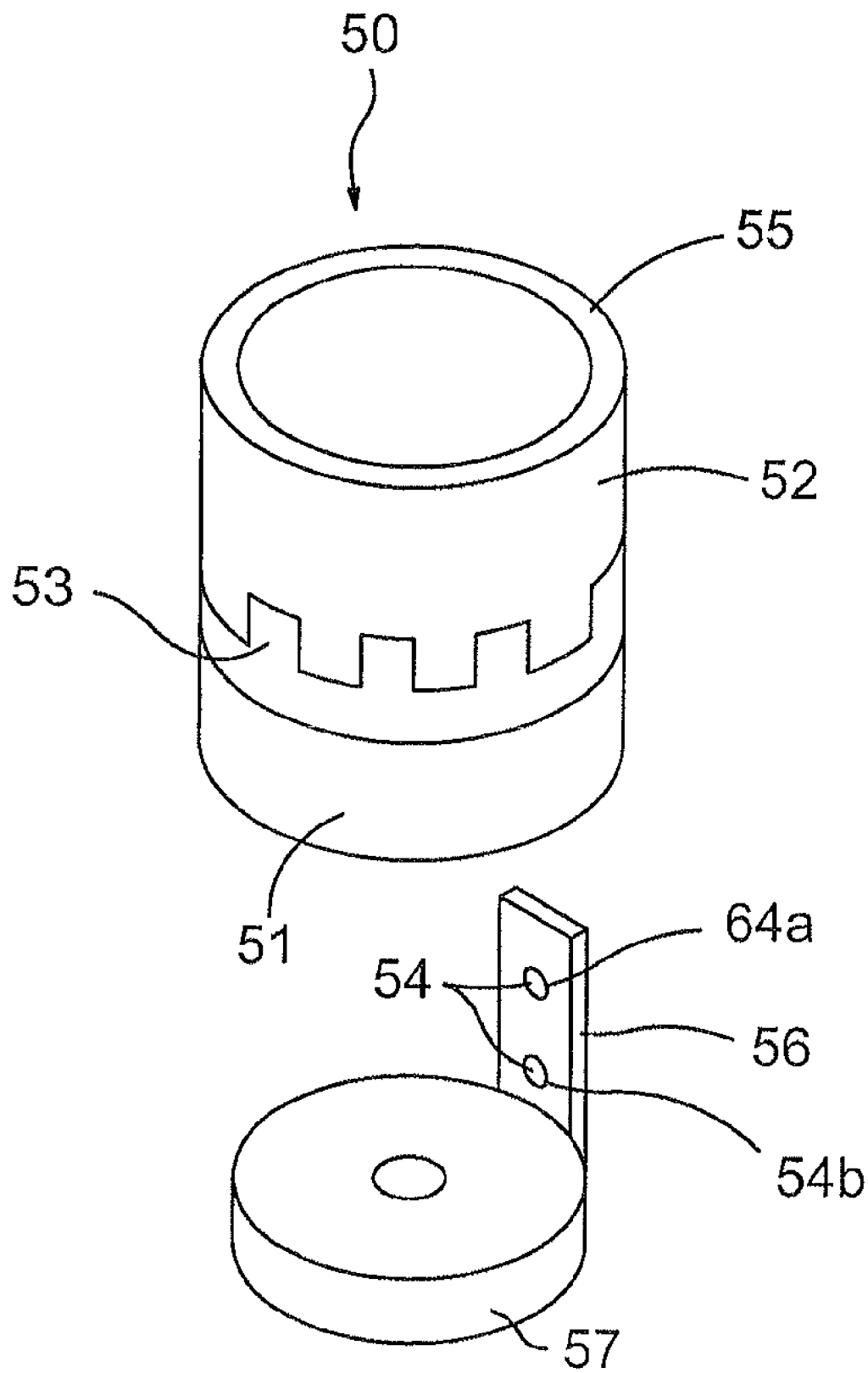
FIG. 16 is a perspective view of a timing mechanism, according to an embodiment of the present invention.

Referring to FIGS. 9A-9B and FIG. 16, the motor 31 actuates a stepping cylinder 50, which has a continuous copper strip 51 on its lower end and an upper copper strip 52 which is perforated by a plurality of apertures 53, which serve as non-conducting windows to stop the upper disk 42 from rotating. The non-conductive portions may be, for example, plexiglass. In addition, it is to be understood that the strips 51 and 52 are not limited to copper, but may be another suitable conductive material. The lower and upper copper strips 51 and 52 are, for example, copper foils cemented to a plexiglass cylinder 55. The upper cooper strip 52 is connected to a positive terminal of a battery, and is powered at all times. The lower copper strip 51 is connected to a positive terminal of the drive motor 31.

The drive motor 31 has two wires connected to a positive side thereof. One wire is from the lower copper strip 51, and another wire is from a positive terminal at the radio control unit. The radio control unit, which is normally in an "off" position, provides a pulse to move the drive motor 31 and contact for the upper foil 54*a* in and out of the apertures 53.

Because the apertures 53 are non-conductive windows, the drive motor 31 stops when the contact for the upper foil 54*a* lines up with the aperture 53. The apertures 53 may be, for example, square or rectangular. The number of apertures is in the ratio of 2:1 with the number of sample tubes 38. Accordingly, if there are four (4) sample tubes 38, there are eight (8) equidistant apertures 53.

Sliding contacts 54 provide the connection from the incoming power to the motor 31. The contacts 54 include the contact for the upper foil 54*a* and the contact for the lower foil 54*b* mounted on a contact support 56. The contact support 56 extends upward from a disc 57, which is made of, for example, plexiglass, and is attached to the drive motor shaft 36 to move the contacts 54 around the plexiglass cylinder 55.

An operation of the stepping cylinder 50 can be described by the following table.

TABLE 1

| Position of Aperture 39 | Position of Upper Contact 54a | Operation |
| --- | --- | --- |
| Over test tube | In first window 53 | Drive motor stopped |
| In motion from over test tube toward the closed position of aperture 39 | In motion from in first window 53 to the copper strip 52 | + pulse from boat activates motor and contact 54a moves onto copper strip 52, passing + pulse to drive motor |
| In motion, then stopping at closed position of aperture 39 | In motion from copper strip 52, then stopping in second window 53 | Drive motor continues until contact 54a enters second window 53 and then stops |
| In motion from closed position of aperture 39, then stopping over next test tube | In motion from second window 53 to copper strip 52, then stopping in third window 53 | + pulse applied to activate motor, moving contact 54a over copper strip 52 until third window 53 is reached and motor stops |

A shutter wheel with windows of non-conductivity can be used as an alternative to employing complex electronic circuitry, while having a simple form of indexing.

Any leaked water can be funneled to the bottom of the cylinder 30 away from the motor 31 by an opening in the platform supporting the motor.

Buoyancy of the vessel can be enhanced by an inner coating of, for example, Styrofoam, which covers the whole area of the hull 6, which is about 30 cm by about 45 centimeters. The hull 6 may be made of, for example, thin steel.

One of the multiple channels of the remote control may be used to raise and lower the cylinder 30. Another channel of the remote control can be used to control the drive motor. The rudder 13 and propulsion motor can be controlled by separate channels on the remote control. Training on how to collect water using this device can be minimal. A tester must momentarily press a switch on a remote control whenever he/she wants the indexing system to rotate in order to sample water from different locations.

The probe 10 can collect a plurality of individual samples in each of the plurality of test tubes at one site in a body of water. The probe 10 can also collect a plurality of individual samples from a plurality of different sites or depths.

The steering mechanism 70 of the boat includes a shaft 71 connected to a steering drive 77 and the rudder 13. The propulsion mechanism includes rotating shaft connected between a boat drive motor 15 and a propeller 14.

The boat may be powered by a solar hydrogen reactor 20, including a plurality of solar panels 1, such as, for example, six (6) 3.0 V, 110 milliamp solar panels 1, wherein four of the solar panels are arranged in series with each other, and the remaining two of the solar panels are arranged in parallel. The solar panels 1 are connected with a plurality of proton exchange membranes (PEMs) 5, such as, four (4) or six (6) 3.0 V fuel cells including the PEMs, also arranged in series with each other. A water cylinder 8, made of, for example, plastic, is connected by tubing 26, such as plastic tubing, to an oxygen cylinder 7 and a hydrogen cylinder 9. The oxygen cylinder 7 is connected, via an oxygen outlet 22 made of, for example, plastic tubing, to the PEMs 5. The hydrogen cylinder 9 is connected, via a hydrogen outlet 23 made of, for example, plastic tubing, to the PEMs 5.

There are two cycles or phases governing the function of the fuel cell reactor; the electrolytic phase and the voltaic phase. The electrolytic phase is endothermic and the voltaic is exothermic.

During the electrolytic phase of operation of the fuel cell reactor 20, the collapsible water cylinder 8 contains no fluids and is maintained under negative pressure. Simultaneously, the oxygen and hydrogen cylinders 7, 9 are completely filled with water and air has been purged from the closed circuit fluid sub-system of the fuel cell reactor 20. Photons from sunlight, which project on the solar panels 1 release electrons from the solar panels. The electrons are conducted by leads to the plurality of PEMs 5. In the PEMs 5, water is split into hydrogen and oxygen. Hydrogen molecules are released from the cathode side of the PEM and oxygen is released from the anode side of the PEM. The hydrogen gas exiting through the hydrogen outlet 23 displaces the water in the hydrogen cylinder 9, and the displaced water is collected in the water cylinder 8, which is maintained under negative pressure. Water in the oxygen cylinder 7 is similarly displaced by oxygen gas exiting through the oxygen outlet 22, and subsequently collected in the water cylinder 8. The electrolytic phase is terminated when the hydrogen and oxygen cylinders 9, 7 are completely filled with hydrogen and oxygen, respectively. The current to the PEMs from the solar panels is then switched off.

During the voltaic phase of operation of the reactor 20, oxygen and hydrogen under atmospheric and hydrostatic pressure are injected into the PEMs 5, where they catalytically combine to produce water and electrical energy. The electrical energy is then used to operate the winch 4, the probe 10, propeller motor 15 and rudder motor 12, by remote control.

The hydrogen cylinder 9 may be, for example, a 1 L bottle to collect the hydrogen gas. The oxygen cylinder 7 may be, for example, a 0.5 L bottle used to collect the oxygen gas. The water cylinder 8 may be, for example, a 2 L bottle used to collect the water displaced from the oxygen bottle 7 and hydrogen bottle 9, when hydrogen and oxygen gas from the PEMs 5 displace the water stored in the oxygen and hydrogen bottles 7, 9.

Accordingly, light energy from the sun, when beamed on the solar panels is converted into electrical energy, and the electricity is then used to split the water in the PEMs 5 into hydrogen and oxygen. The water bottle 8 maintained under sub-atmospheric pressure pulls water displaced from the oxygen and hydrogen bottles 7, 9, as these are filled with oxygen and hydrogen gas. The hydrogen and oxygen are then catalytically combined in the PEMs 5 and the electrical energy generated used to power the boat.

During the electrolytic phase, energy from the sun is converted to electricity, which is used for the electrolysis of water into hydrogen and oxygen. In the voltaic phase, the stored hydrogen and oxygen are catalytically combined in the PEMs 5. The electrons released from this exothermic reaction can be used for work, including free energy for the operation of motors, such as motors 12 and 15, the winch 4 and/or a robotic arm.

The drone boat and its sub-components can be powered by, for example, solar electrical energy and solar hydrogen electrical energy. In utilizing solar energy, the solar panels convert the sunlight to electrical energy, which is used to power the motors and also stored in a rechargeable battery. The solar hydrogen electrical (sHe) energy is derived from the catalytic combination of hydrogen and oxygen in the PEMs 5.

The boat may use distilled water as a fuel. Alternatively, the boat and its motors may be powered by conventional combustion or steam engines.

The reactor 20 can produce 12 V and 440 milliamps in order to satisfy all of the components. The hydrogen outlets of each PEM 5 are connected to each other by air lines, such as, for example, flexible plastic air lines. The oxygen outlets are similarly connected. The tubes connecting the hydrogen outlets are joined to a common tube which terminates in the hydrogen bottle 9, which is initially filled with distilled water. The tubes originating from the oxygen outlets of the PEMs 5 are joined to a common tube which terminates in the oxygen bottle 7, also initially filled with distilled water.

The solar panels 1 are connected to the PEMs 5 in series and the PEMs are primed by distilled water in a 15 ml syringe and a plastic needle. Air bubbles are purged from the system.

Although exemplary embodiments of the present invention have been described hereinabove, it should be understood that the present invention is not limited to these embodiments, but may be modified by those skilled in the art without departing from the spirit and scope of the present invention, as defined in the appended claims.

What is claimed is:
1. A water sampling device, comprising:
 a cylinder;
 a first disk positioned at a top of the cylinder;
 a plurality of sampling tubes attached to the first disk;
 a second disk positioned on the first disk, wherein the second disk includes an aperture through which water to be sampled flows into one of the plurality of sampling tubes when the aperture is lined up with an opening of the one sampling tube, wherein the cylinder is submerged to allow the water to be sampled to flow through the aperture, wherein the second disk rotates to line up the aperture with the opening of the one sampling tube;
 a timing mechanism controlling rotation of the second disk the timing mechanism comprising;
  a first conductive strip;
  a second conductive strip, wherein the second conductive strip is perforated by a plurality of apertures creating non-conductive spaces between non-perforated portions of the second conductive strip;
  a first contact contacting the first conductive strip; and
  a second contact alternately contacting the second conductive strip and the non-conductive spaces; and
 a motor for rotating the second disk, wherein the motor is disengaged when the second contact contacts a non-conductive space.

2. The water sampling device according to claim 1, wherein water to be sampled flows into another of the plurality of sampling tubes when the aperture is lined up with an opening of the other sampling tube.

3. The water sampling device according to claim 2, wherein the second disk rotates the aperture away from the opening of the one sampling tube to line up the aperture with the opening of the other sampling tube.

4. The water sampling device according to claim 1, wherein the second disk is coupled to a shaft rotated by the motor.

5. The water sampling device according to claim 4, wherein the motor is remotely controlled.

6. The water sampling device according to claim 1, wherein the first disk is fixed to the cylinder and remains stationary while the second disk rotates.

7. The water sampling device of claim 1, wherein the plurality of sampling tubes are attached to the first disk at a side opposite to the side on which the second disk is positioned on the first disk.

8. A method for water sampling, comprising:
 positioning a first disk at a top of a cylinder, wherein a plurality of sampling tubes are attached the first disk and extend from an underside of the first disk;
 positioning a second disk on a top side of the first disk, wherein the second disk includes an aperture;
 lining up the aperture with an opening in one of the plurality of sampling tubes;
 submerging the cylinder to allow water to be sampled to flow through the aperture into the opening of the one sampling tube;
 rotating the second disk to line up the aperture with the opening of the one sampling tube, wherein rotation of the second disk is controlled by a timing mechanism comprising:
  a first conductive strip; and
  a second conductive strip perforated by a plurality of apertures creating non-conductive spaces between non-perforated portions of the second conductive strip;

contacting the first conductive strip with a first electrical contact; and alternately positioning a second electrical contact to contact the second conductive strip and the non-conductive spaces.

9. The method according to claim 8, further comprising rotating the second disk to move the aperture away from the opening of the one sampling tube to line up the aperture with an opening of another of the plurality of sampling tubes.

10. The method according to claim 8, further comprising remotely controlling a motor to rotate a shaft coupled to the second disk.

11. The water sampling device according to claim 8, wherein the first disk is fixed to the cylinder and remains stationary while the second disk rotates.

12. The method according to claim 8, wherein a motor for rotating the second disk is disengaged when the second electrical contact contacts a non-conductive space.

* * * * *